United States Patent [19]

Beauvais et al.

[11] 4,406,861
[45] Sep. 27, 1983

[54] MICROWAVE CANNING APPARATUS

[76] Inventors: Max P. Beauvais, 46 Southridge West, Tiburon, Calif. 94920; Raymond E. Camezon, 623 Tunbridge Rd., Danville, Calif. 94526

[21] Appl. No.: 356,222

[22] Filed: Mar. 8, 1982

Related U.S. Application Data

[63] Continuation-in-part of Ser. No. 336,676, Jan. 4, 1982, which is a continuation-in-part of Ser. No. 305,279, Sep. 24, 1981, which is a continuation of Ser. No. 122,354, Feb. 19, 1980, abandoned.

[51] Int. Cl.³ .......................... A61L 2/06; A61L 2/12; A23L 3/10
[52] U.S. Cl. ..................... 422/113; 99/369; 99/451; 219/10.55 R; 219/10.55 E; 422/21; 422/26; 422/293; 422/296; 422/299; 422/302; 426/234; 426/241; 426/403; 426/407
[58] Field of Search ............. 426/234, 403, 407, 107, 426/401, 397, 241, 243; 99/369, 45, 483; 219/10.55 R, 10.55 E, 10.55 M; 422/26, 21, 113, 293, 296, 299, 302

[56] References Cited

U.S. PATENT DOCUMENTS

| | | |
|---|---|---|
| 676,869 | 6/1901 | Bourdeau . |
| 947,062 | 1/1910 | Hawkins . |
| 1,197,646 | 9/1916 | Meierjohann . |
| 1,524,623 | 1/1925 | Landrum et al. . |
| 1,621,132 | 3/1927 | Reinbold . |
| 2,457,867 | 1/1949 | Chambers . |
| 2,555,230 | 5/1951 | Ford . |
| 3,494,722 | 2/1970 | Gray ................................. 422/21 |
| 3,561,982 | 2/1971 | Oeth . |
| 3,753,651 | 8/1973 | Boucher ........................... 422/21 |
| 3,840,686 | 10/1974 | Hurwitz . |
| 3,875,318 | 4/1975 | Davies . |
| 3,949,934 | 4/1976 | Goglio . |
| 4,051,972 | 10/1977 | Botkin . |
| 4,103,431 | 8/1978 | Levinson . |

OTHER PUBLICATIONS

Modern Plastics Encyclopedia, 1971–1972, vol. 48: No. 10A, Oct. 1971, McGraw Hill, Inc. NY, pp. 3, 105–106.

Primary Examiner—Barry S. Richman
Attorney, Agent, or Firm—Limbach, Limbach & Sutton

[57] ABSTRACT

A method and apparatus for canning food products in a non-metallic jar, utilizing a metallic or non-metallic jar lid and a non-metallic enclosure enveloping the jar and lid and which is placed within a microwave oven for heating with a pressure control check valve for limiting the maximum pressure within the enclosure during heating and preventing entry of air during subsequent cooling of the enclosure and food product.

5 Claims, 4 Drawing Figures

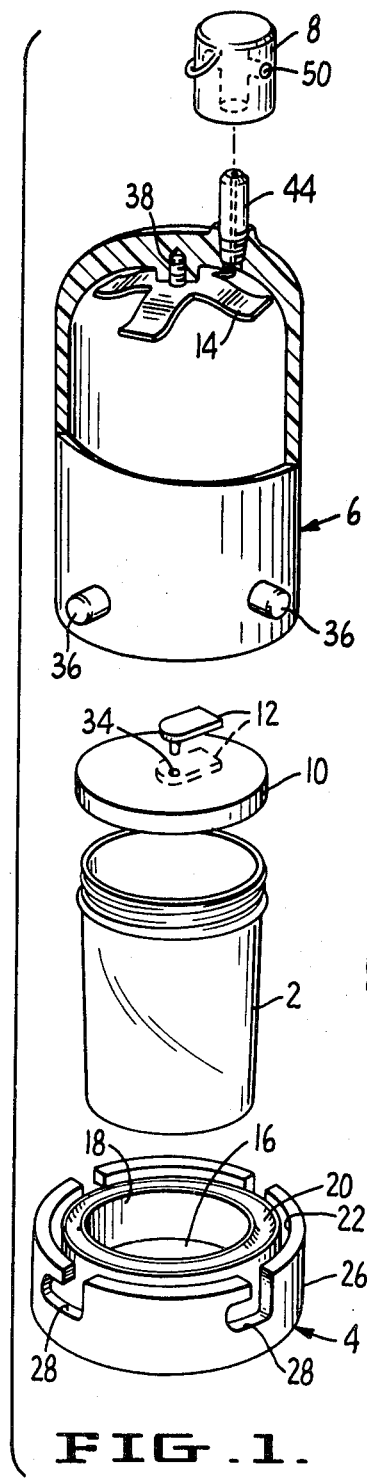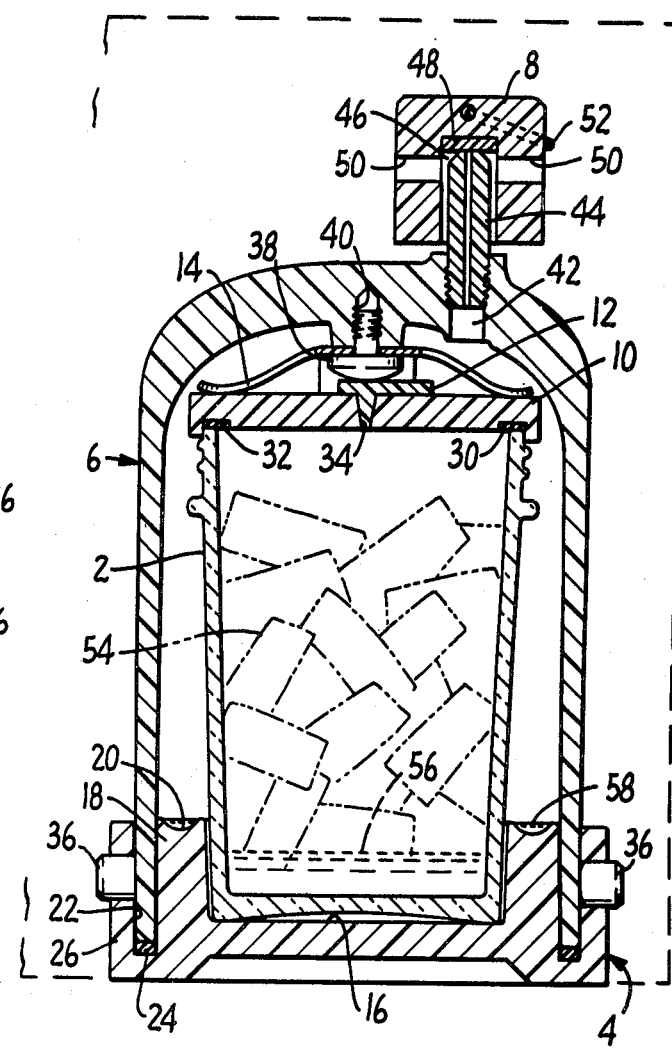

U.S. Patent  Sep. 27, 1983  Sheet 2 of 2  4,406,861
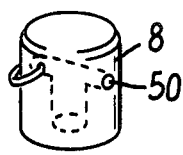
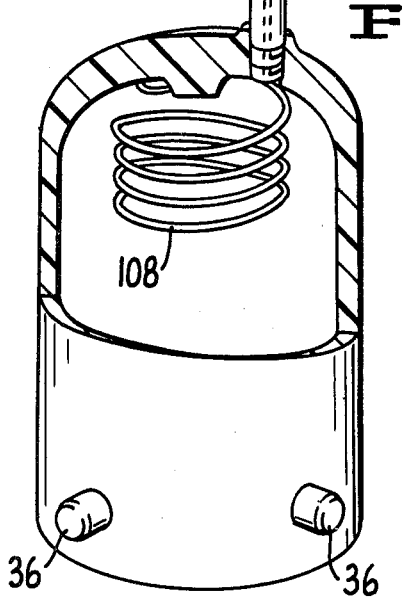
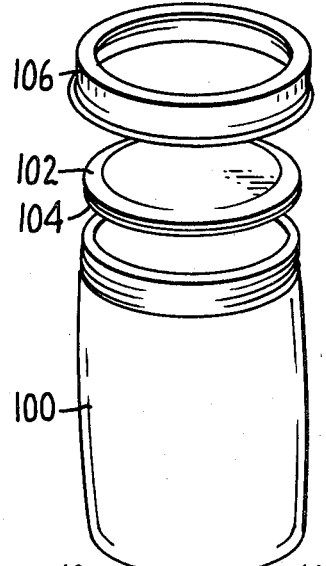
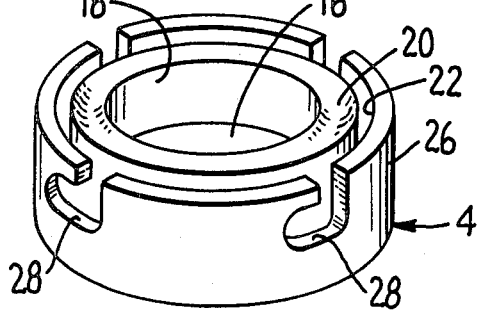
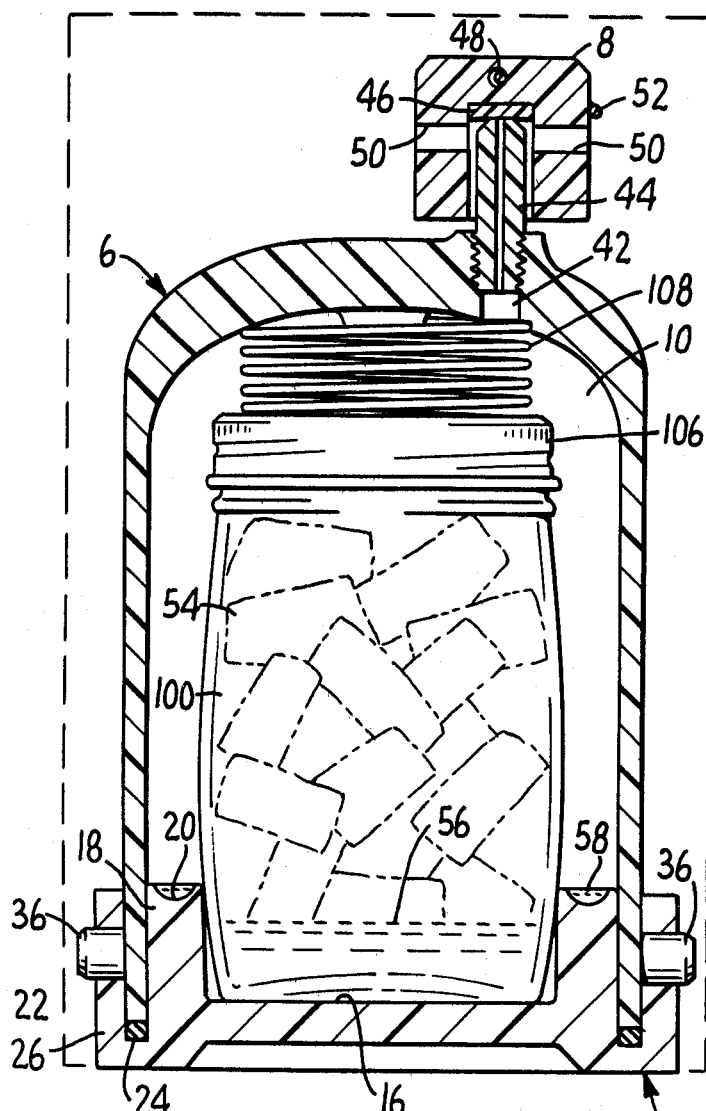
FIG. 3.
FIG. 4.

MICROWAVE CANNING APPARATUS

RELATED APPLICATIONS

This application is a continuation-in-part of patent application Ser. No. 336,676, filed Jan. 4, 1982 which is a continuation-in-part of patent application Ser. No. 305,279, filed Sept. 24, 1981 which is a continuation of patent application Ser. No. 122,354, filed Feb. 19, 1980 now abandoned.

BACKGROUND OF THE INVENTION

This invention relates to methods and apparatus for canning food products. More particularly, it relates to methods and apparatus which are suitable for use in home canning operation. Even more particularly, the invention relates to such methods and apparatus which are suitable for use with a home microwave oven.

Home canning of various types of produce, such as fruits and vegetables, has been a popular activity in the United States. While there are many attractive reasons for such home canning, a major disadvantage to the procedure has always been the necessity for pressure cooking the food product within the container. This process has generally involved preparing the food products and placing them in containers, such as glass jars with loosely closed tops, and then placing the container and product within a pressure cooking vessel, or retort, and then applying steam to the containers and their contents for an extended period of time within the pressure cooker, to cook and sterilize the food.

The conventional apparatus and methods for home canning have suffered from a number of disadvantages which have discouraged many people from engaging in the home canning process. The disadvantages have included the necessity for expensive and bulky pressure cooking apparatus and the requirement of substantial time and heating energy to perform the pressure cooking procedure. These requirements have made home canning economically practical only when conducted on a substantial scale. Furthermore, pressure cooking of certain fruits and vegetables in the canning process destroys many desirable characteristics of the food, including crisp textures and retention of vitamins within the fruits and vegetables themselves.

A far simpler approach to this home canning process is disclosed in U.S. Pat. No. 4,294,167, issued Oct. 13, 1981 in the name of Max P. Beauvais, one of the co-inventors herein. Such patent discloses a simpler apparatus for use in stove top canning operations.

In recent years the home microwave oven has enjoyed an enormous growth in popularity, largely because of the speed with which it cooks, generally taking about one fourth the time of conventional oven cooking. Although the microwave oven has provided for rapid cooking, it has not been suitable for use in conventional home canning operations for several reasons. One reason is the enormous absorption of microwave energy by any metallic objects placed within the oven cavity, such that those metallic objects would absorb a great proportion of the microwave energy, thus reducing that available for sterilizing and preparing the food. For this reason, it is generally considered highly inadvisable to place any metallic objects within a microwave oven when it is operating. However, in certain circumstances some metallic objects can be used in the microwave ovens without experiencing these characteristic problems associated with metallic objects in microwave ovens. Conventional home canning apparatus is almost entirely of metallic construction. Accordingly, none of this apparatus is suitable for use in microwave ovens except that the use of metallic lids has been found to be feasible in certain situations. Further, even if the conventional apparatus were fabricated of a material suitable for use in a microwave oven, the relatively small (generally one cubic foot) volume of most microwave ovens precludes the use of the bulky conventional apparatus. Accordingly, until now there has been no satisfactory apparatus for convenient home canning, which can take advantage of the rapid heating of a microwave oven.

SUMMARY OF THE INVENTION

To overcome the foregoing and other disadvantages of prior art canning methods and apparatus, it is an object of the present invention to provide such methods and apparatus which are fast and simple to use.

It is another object of the invention to provide such method and apparatus which are suitable for use in microwave ovens.

It is a further object of the invention to provide such methods and apparatus in which the food products may be sterilized within the microwave oven quickly and without the texture-destroying and vitamin-destroying prolonged pressure cooking and which may provide for storage with a high vacuum within the canning container to avoid spoilage caused by the presence of oxygen.

To achieve these and other objects, which will become apparent below, the canning apparatus is provided for canning food products in non-metallic jars, which includes a jar lid which can be constructed of a metallic or non-metallic material. There is a seal on the lid for engaging the mouth of the jar and forming an air-tight seal therewith under the influence of greater atmospheric pressure outside the jar than inside, and an enclosure of non-metallic material substantially transparent to microwave energy for enveloping the jar and lid. This enclosure includes a base member for engaging the base of the jar and holding it in a predetermined position, a cover member releasably engaging the base member and enclosing at least the portions of the jar and lid not enclosed by the base member, a resilient structure for urging the jar lid against the jar mouth, and a pressure control check valve communicating with the interior of the enclosure for limiting the maximum pressure within the enclosure to a predetermined amount above the ambient pressure outside while preventing any inflow of air from the outside.

In situations where a conventional metallic lid and metallic ring are used, the resilient structure for urging the lid against the jar mouth functions to maintain the position of the jar in the enclosure. The lid is urged against the jar mouth by the metallic ring.

A method of sterilizing and canning food products within non-metallic jars and without substantial cooking thereof is provided and includes the steps of placing the food products into such a jar with a small quantity of liquid sufficient to cover the bottom of the interior of the jar, placing a metallic or non-metallic lid having a structure capable of an air-tight seal over the mouth of the jar, enclosing the jar and lid within an enveloping air-tight non-metallic enclosure having a one way check valve for permitting expulsion of air and steam from the enclosure, and the enclosure having a structure for resiliently urging the lid against the mouth of the jar, applying sufficient microwave energy to the enclosure jar and food products to convert at least a substantial portion of the liquid into steam to sterilize the food products and fill the jar and interior of the enclosure with steam of a predetermined pressure for a predetermined period of time, removing the microwave energy and applying a cooling fluid to at least the lower portions of the exterior of the enclosure while preventing entry of fluids into the enclosure interior, to cool the enclosure and its interior, and then venting the enclosure interior to ambient pressure.

The method of sterilizing and canning food products in another embodiment sets forth that when a metallic lid and metallic ring are used, the ring urges the lid against the mouth of the jar and a resilient means attached to the enclosure bias against the lid to hold the lid, ring and jar in position within the enclosure.

BRIEF DESCRIPTION OF THE DRAWINGS

One preferred and other embodiments of the apparatus of this invention will be described in detail in which:

FIG. 1 is an exploded perspective view thereof, partially in section, and

FIG. 2 is a side sectional view of the assembled apparatus of FIG. 1, such section being taken through the center of the apparatus.

FIG. 3 is an exploded perspective view partially in section of the apparatus using a standard Mason jar and metallic lid and ring.

FIG. 4 is a side view of the assembled apparatus of FIG. 3, such section being taken through the center of the apparatus.

DETAILED DESCRIPTION OF THE PREFERRED EMBODIMENT

The basic apparatus of the present invention is illustrated in FIGS. 1 and 2 and includes generally a jar 2, which may suitably be a conventional canning jar of pint, quart, or other desired capacity, enclosure base 4 and enclosure cover 6 and pressure regulating weight 8. Also provided are jar lid 10, jar lid vent closure 12 and jar lid biasing spring 14.

While the jar 2 is conventionally made of glass, the base member 4, cover 6, pressure regulating weight 8, jar lid 10 and biasing spring 14 may be formed of any of a number of suitable non-metallic materials. However, it has been found that the jar lid 10 can be constructed of a metallic material and not cause any problem in practicing the invention (to be discussed later). One suitable non-metallic material is a polysulfone synthetic resin, although other known materials having the desired characteristics may readily be substituted. Although metallic jar lids are not transparent to microwave energy, certain types can be successfully used without any problems. The vent closure 12 may suitably be fabricated of an appropriate silicone rubber, or the like.

The base member 4 preferably is of a circular configuration, as shown in FIG. 1, with a recess 16 in its center. This recess 16 is preferably configured and dimensioned to receive and position a canning jar, such as a Mason jar of pint or quart size. In the upper surface of the ring 18 surrounding recess 16 there preferably is provided a shallow groove 20, for purposes to be described below.

Outside the ring 18 is a deep groove 22 having an O-ring sealing member 24, suitably of a silicone rubber or similar compressible material at its base. Outside groove 22 is outer ring 26, having a plurality of L-shaped cutouts 28, to form the sockets for a bayonet mount to be described below.

The jar lid 10 in the primary embodiment of the invention is of a suitably formed, rigid non-metallic material, such as a synthetic resin, includes a groove 30 in its underside, within which is provided a resilient gasket 32, of a material suitable for forming an air-tight seal between the lid 10 and the mouth of the jar 2. In a second embodiment of the invention the jar lid 10 is made of a metallic material (FIG. 3). The metallic lid also has resilient gasket similar to 32 attached for forming an air-tight seal between the lid and the mouth of the jar. Extending through the lid 10 is a vent hole 34, which suitably may be conically tapered as shown in FIG. 2. The removable closure 12 includes a portion insertable into the vent hole 34 for blocking the vent hole to prevent entry of air through that hole except when the closure 12 is removed.

Cover member 6 may suitably be of the generally bell-shaped configuration shown in FIGS. 1, 2, 3 and 4. Spaced circumferentially around the cover adjacent its open lower end are a plurality of bosses 36, positioned to cooperate with the L-shaped slots 28 to form a "bayonet" mount to assemble and lock the cover 6 and base 4 together. In the assembled configuration, shown in FIGS. 2 and 4, the lower portion of the cover 6 is received into the base groove 22 and bears firmly against the sealing member, or O-ring, 24 to form an air-tight seal between the cover 6 and base member 4.

Preferably, the interior of the cover 6 is configured and dimensioned to fit relatively closely around a jar and lid positioned within the recess 16 in the base member 4, as shown in FIG. 2. Connected to the upper portion of the interior of the cover 6 is resilient leaf spring 14, also made of a suitable non-metallic material. In the primary embodiment the leaf spring is configured as shown in FIG. 2. In a second embodiment of the invention the spring attached to cover member 6 has a coil configuration (see FIGS. 3 and 4). The leaf spring 14 may suitably be attached to the cover 6 by a resilient plug 38, which may be threaded or force fitted into a recess 40 in the cover 6. As shown in FIG. 2, the cover 6 is dimensioned such that, when assembled with the base 4 to form the enveloping enclosure, the spring 14 resiliently urges the jar lid 10 against the mouth of the jar 2. In this assembled configuration the plug 38 resiliently presses against the closure 12, also serving to urge the lid 10 against the jar mouth.

An aperture 42 is provided through the cover 6, suitably with a tube 44, of synthetic resin, inserted thereinto, as by threading. This tube 44 provides for venting the interior of the enclosure when desired.

Weighted pressure regulating member 8 includes a recess 46 for receiving tube 44 thereinto, and has a sealing gasket 48 at the base of the recess 46, for resiliently sealing against the open outer end of the tube 44 under the weight of the member 8. A pair of ports 50 communicate with the recess 46 to provide for venting pressurized fluids escaping through the interior of the tube 44. If desired, a bail 52 may be provided for lifting the weighted member 8.

A second embodiment of the invention is shown in FIGS. 3 and 4. The primary structural features of base member 4 and cover 6 are the same as previously described for the primary embodiment of the invention. Base member 4 is of a generally circular configuration with a recess 16 in the center. Recess 16 is preferably configured and dimensioned to receive and position a canning jar. The upper surface of the ring 18 surrounding recess 16 is providing a shallow groove 20. The deep groove 22 having an O-ring sealing member 24 therein disposed is used for sealing the cover 6 and base member 4. Outside groove 22 is an outer ring 26 having a plurality of L-shaped cut-outs 28 which form sockets for a bayonet engagement with members 36 of the cover 6.

The cover 6 is configured and dimensioned to fit relatively closely around the jar and lid positioned within the recess 16 of base member 4, as shown in FIG. 4. Connected to the upper portions of the interior of cover 6 for the second embodiment, is a resilient coil spring 108 for urging the lid against the jar mouth. The cover 6 has members 36 for fitting in openings of base member 14 for a bayonet type locking enclosure.

As shown in FIG. 3, a standard Mason type jar is used. The Mason jar 100 is fitted with its conventional type of closing members lid 102 having sealing member 104 and ring 106 which threadedly engages jar 100.

The cover 6 still has thereon disposed the pressure assembly consisting of tube 44 and pressure cap 8 having opening 50 for release of pressure. The operation and description of this assembly used in conjunction with cover 6 is the same for the second embodiment as was previously described for the primary embodiment.

Generally shown at FIG. 4 is the base member 4 with the cover 6 locked in position. The spring 108 is depressed against lid 102 and ring 106, which is threadably engaged to jar 100. The ring 106 which readily engages jar 100, is hand tightened down on jar 100. The remainder of the numbered areas, as shown in FIG. 4 are the same as were described for the primary embodiment in FIGS. 1 and 2. In the remainder of the disclosures except where otherwise indicated, jar 100 and jar 2 are interchangeable and, the lid 102 is interchangeable with lid 10. However, it is to be noted that lid 102 is constructed of a metallic material. Further, the description referring to urging means 14 is interchangeable with the action of coil spring 108. The disclosure of the method of operation of the apparatus, which follows is the same for both the primary and secondary embodiments of the apparatus as shown in FIGS. 2 and 4, except in the secondary embodiment the ring 106 with lid 102 is screwed on hand tight to jar 100 and when heated by the microwave the air and steam escape through the hand tightened lid and ring versus escape through hole 34 in lid 10 in the primary embodiment.

The secondary embodiment describes the function of the coil spring 108, as urging the lid 102 against the mouth of jar 100. In certain types of canning this method of urging the lid by spring 108 will not be sufficient for the desired end result. This method of urging the lid is sufficient where there is only a small amount of liquid is placed in the bottom of jar 100. When subjected to microwaves, this liquid will flash into steam, expand and push the air and some of the steam from within the jar. However, when it is desired to conventionally brine pack or syrup pack food products, a large amount of fluid will be lost if the coil spring urging means is relied on to bias the lid against the jar mouth.

When it is desired to brine or syrup pack food products, the above described urging means 14 or 108 will allow a substantial amount of the brine or syrup to escape from the jar. In situations when it is desired to retain the brine or syrup with the food product, the means by which this is done is with metallic ring 106.

The metallic ring 106 will urge the lid 102 against the mouth of jar 100 such that it will allow the air and some steam to be evacuated from the jar when the food product is subjected to microwave energy. The ring 106 holding the lid 102 will not, however, allow any substantial amounts of the brine or syrup to escape when the jar is subjected to microwave energy.

The urging means 14 or 108 have the function of only holding the jar 100 with the lid 102 and ring 106 in position in recess 16 in the enclosure. If this is the case, when and if the enclosure containing the jar 100 is tipped over, the jar 100 will not slide out of recess 16 and at all times will be firmly biased in position, as shown in FIG. 4.

In the previously described embodiments of the apparatus of the invention it has been set forth that either a leaf spring (14) or resilient coil spring (108) is to be used to resiliently urge the metallic or non-metallic lid or the lid and ring combination against the mouth of the jar. It has also been set forth that when it is desired to brine or syrup pack food products, the lid is urged by the ring alone and the resilient urging means is a resilient holding means which works in conjunction with the ring. However, the inventor contemplates that the invention can be practiced without the need for any type of resilient urging means for either resiliently holding the ring and lid in place or for merely providing proper urging necessary when the ring is used for urging the lid. When there is no resilient urging means used, the lid 102 will be urged against the mouth of the jar by ring 106 with no other structure contacting or impacting lid 102 having ring 106 threadably engaging the mouth of jar 100.

It is contemplated that both the lid and ring can be constructed of a metallic material or non-metallic material. It is also contemplated that the ring can be metallic and the lid non-metallic and vice-versa and the invention can still be properly practiced. In situations where it is desired to have the ring metallic and the lid non-metallic (and vice-versa) it is contemplated that there may be some spacing between the lid and ring during certain phases of the practicing of the invention and when the lid and ring are made of these different materials, it will prevent any interaction between the lid 102 and ring 106.

It is found that this embodiment of the invention not employing the use of a resilient urging means does not prevent or establish any different working parameters for the apparatus and involved method of this invention. As such it will be found that the jar 100 will be free standing in base 16 and all other operations as previously described can be conducted as per the described apparatus and method throughout this application.

The apparatus of this invention having been described above, a preferred method of its use may be seen. Into the non-metallic container 2 (or 100), suitably a glass canning jar, may be placed the food products 54 to be canned, for example, fresh fruits or vegetables (FIG. 2 and FIG. 4). Either before, concurrently with, or after placing the food product 54 into the jar 2 (or 100), a small amount of liquid 56 is placed into the jar, the amount needing to be sufficient only to cover the bottom of the jar. This liquid 56 may suitably be an aqueous solution or juices from the food product. The lid 10 is then placed loosely over the mouth of the jar and the jar and lid combination placed into the recess 16 of the base 4. In the secondary embodiment the lid 102 is placed on the mouth of jar 100 and the ring 106 is screwed hand tight on jar 100 and the combination is placed in recess 16 of base 4. A small amount, suitably a fraction of an ounce, of water 58 is placed in the groove 20 in the base 4. At this point the cover member 6, with its pressure regulating weight 8, is then assembled with the base 4, inserting the lower portion of the cover into the base groove and the bosses 36 into the L-shaped slots 28, while providing pressure, and then turning the cover sufficiently to lock the base and cover together. This engagement, with the base of the groove 22 and the lower edge of the housing 6 compressively engaging the sealing member 24, forms an enveloping, air-tight enclosure. The tube 44 with the pressure regulating weight 8 also forms a one-way check valve for permitting expulsion of air and steam from the enclosure while preventing any back flow of air into the enclosure.

The method of sterilization and canning is also accomplished by the following method when it is desired to retain the brine or syrup pack with the food product. Into the non-metallic container 100, suitably a glass canning jar, may be placed the food products 54 to be canned, for example, fresh fruits or vegetables (FIG. 2 and FIG. 4). Either before, concurrently with, or after placing the food product 54 into the jar 100, the brine or syrup pack is placed into the jar. The lid 102 is then placed loosely over the mouth of the jar and ring 106 is tightened over the lid 102. The ring threadably engages the jar 100 and the jar lid, and ring combination placed into the recess 16 of the base 4. A small amount, suitably a fraction of an ounce, of water 58 is placed in the groove 20 in the base 4. At this point, the cover member 6, with its pressure regulating weight 8, is then assembled with the base 4, inserting the lower portion of the cover into the base groove and the bosses 36 into the L-shaped slots 28, while providing pressure, and then turning the cover sufficiently to lock the base and cover together. This engagement, with the base of the groove 22 and the lower edge of the housing 6 compressively engaging the sealing member 24, forms an enveloping, air-tight enclosure. The tube 44 with the pressure regulating weight 8 also forms a one-way check valve for permitting expulsion of air and steam from the enclosure while preventing any back flow of air into the enclosure.

As shown in FIG. 2, the assembly of the cover 6 and base 4 also brings the spring member 14 attached to the cover 6 into resilient engagement with the upper surface of the lid 10, thus urging the lid 10 against the mouth of the jar. Similarly, the attaching plug 38 engages the removable closure 12 on the lid and further resiliently urges the lid against the jar mouth.

In FIG. 4, the assembly of the cover 6 and base 4 brings coil spring 106 into resilient engagement with the upper surface of lid 102 and ring 106.

When a brine or syrup pack is desired to be retained, the assembly of cover 6 and 4 bring the coil spring 108 (or 14) into engagement with the upper surface of lid 102 and ring 106. This engagement is to hold jar 100 with lid 102 and ring 106 in position in the assembly.

The apparatus assembled as described is then placed into a microwave oven and microwave energy is applied thereto. Since the jar and enclosure are formed of materials which are generally transparent to microwave energy, most of that energy directed against the apparatus is passed directly therethrough and is available for heating the food product 54, liquid 56 and water 58. Since the water 58 in the shallow groove 20 is very shallow and is not shielded by the food product from the microwave energy, which is commonly directed from above, this water 58 will quickly vaporize into steam. The expansion of this steam will serve to expel the air between the lidded jar and the interior of the enclosure, driving it out the exhaust tube 44, the pressure of the steam lifting the weighted member 8 sufficiently to allow such expulsion. Continued heating, even for a very few minutes, will quickly convert a portion of the liquid 56 within the jar into steam, causing that steam to pass up through the food product 54 to sterilize the food product, even without substantial cooking thereof. In the primary embodiment, the expansion of this steam within the jar 2 will then force the lid 10 upwardly against the resilient urging of the spring 14 and button 38 to allow the steam to escape between the gasket 32 on the lid and the mouth of the jar into the interior volume of the enclosure surrounding the jar.

In the secondary embodiment the expansion of this steam within jar 100 will force lid 102 upwardly against the resilient urging of the spring 108 and steam will escape where the lid contacts the ring 106 near the jar mouth. The spring 108 keeps the jar 100, lid 102 and ring 106 in place and does prevent the lid 102 and ring 106 from coming off if they are not screwed on by mistake. The expansion and escape of the steam from within the jar also serves to drive substantially all air from within the lidded jar, helping to prevent subsequent spoilage. Steam pressure above the desired predetermined maximum pressure again escapes out tube 44 past the gasket 48 and out the ports 50 of pressure regulating weight 8.

When the brine or syrup pack is desired to be retained, the microwave energy will heat the food product and brine or syrup pack in jar 100. The expansion of the steam created by the expansion of the fluid will force lid 102 upwardly into ring 106 and air and a small amount of steam will escape around the lid and ring but almost all of the brine or syrup pack will be retained in jar 100 with the food product. The spring 108 will hold the jar 100, lid 102 and ring 106 firmly in recess 16 during the whole operation. The expansion of the fluid into steam will cause substantially all of the air to be driven from the jar 100 helping to prevent subsequent spoilage.

Once the predetermined pressure and temperature are reached, as evidenced by the steam escaping out ports 50 of the pressure regulating weight 8, the sterilizing process may be continued for a predetermined desired time, typically only a very few minutes with the uniform heating of a microwave oven. At the completion of this time, the microwave energy is removed and the entire apparatus may be removed from the microwave oven for cooling. This cooling suitably may be performed by applying a cooling fluid to the apparatus, as by placing the entire apparatus into either standing or running water sufficient to cover the lower portion of the enclosure, without the water extending above the opening of the vent tube 44. Since the cooling will thus take place most quickly from the outside inwardly, any steam remaining between the jar and the interior of the enclosure will quickly be condensed, substantially lowering the pressure within the interior of the enclosure. By virtue of the one-way check valve formed by the action of the weight 8 and its gasket 48 over the outlet of vent tube 44, there can be no inflow of air into the enclosure as long as the weight 8 remains in place. Also, since the volume between the jar and the interior surface of the enclosure will be cooled before the interior of the lidded jar, the pressure will be reduced outside the jar more quickly than inside. This pressure reduction will thus tend to draw out the remaining steam from within the jar and effect an evaporative or vacuum cooling of the contents of the jar. This evaporative cooling will continue until the pressure differential between the interior and exterior of the jar is reduced to a level that the engagement between the lid and the jar mouth will permit no further flow, thus indicating substantial cooling of the interior of the jar with its resulting reduced steam pressure. Such sufficient cooling may take only a very few minutes.

After this brief cooling by the application of the cooling fluid to the exterior of the enclosure, the apparatus may be removed from the cooling fluid and the pressure regulating weight 8 lifted off the end of tube 44. The removal of this weight 8 thus effects a sudden venting of the interior of the enclosure to the surrounding atmosphere, providing for further cooling within, and causing the pressure differential effected by the substantially reduced pressure, on the order of a 30 to 40 torr vacuum, within the jar 2 or 100 to urge the lid 10 or 102 and its gasket 32 or 104 respectively firmly against the mouth of the jar into an air-tight seal with the jar mouth. For the primary embodiment the engagement of the closure 12 within the vent hole 34 prevents air leakage through that vent hole. After venting the interior of the enclosure to ambient pressure, the cover 6 may then be disassembled from the base 4 by giving it a slight turn counterclockwise, when viewed from above, and lifting it to disengage the bosses 36 from the base slots 28. At this point the canning procedure is substantially complete and the lid 10 or 102 will remain firmly sealed against the mouth of the jar 2 by virtue of the greater atmospheric pressure outside the jar than inside.

When it is desired to open the jar 2 or 100 for removal of the food product from within, it may easily be done in any of several ways. If it is desired to heat the food product, the sealed jar may be heated, by placing it in hot water or otherwise, to increase the pressure within. When the pressure within the container is substantially equalized with the ambient pressure, the lid 10 or 102 may simply be lifted off. Due to the high vacuum within the container, this heating and its creation of steam within the container may be done very quickly, often in only one or two minutes. Alternatively for the primary embodiment, if it is not desired to heat the product, such as where fruit is desired to be served cold, the closure 12 may be pulled free from its engagement within the vent hole 34, thus venting the interior of the jar 2 to atmospheric pressure, and again permitting lifting off of the lid 10. This closure 12 may be reused in a subsequent canning procedure by simply reinserting it into the vent hole 34 of the lid to be used.

While the foregoing describes a particularly preferred embodiment of the method and apparatus of the present invention, it is to be recognized that numerous variations and modifications of this apparatus and method, all within the scope of the invention, will readily occur to those skilled in the art. Accordingly, the scope of the invention is to be limited solely by the claims appended hereto and not by the description of the preferred embodiment.

We claim:

1. An apparatus for use in a microwave oven for canning food products in a non-metallic comprising:
   a non-metallic jar having a mouth;
   a compressible gasket means;
   a jar lid having sealing means for engaging the mouth of the jar and forming an air-tight seal therewith under the influence of greater atmospheric pressure outside the jar than inside;
   a ring which threadably engages the top portion of the non-metallic jar and urging the jar lid against said jar mouth, and
   an enclosure of non-metallic material generally transparent to microwave energy enveloping said jar and said lid and comprising
   a base member for supporting said jar;
   a cover member releasably engaging said base member with said gasket means compressively positioned therebetween, and enclosing at least the portions of said jar and said lid not enclosed by said base member, said cover member, gasket means, and said base member forming a pressure-tight seal therebetween when so engaged, as to prevent the entry of gas from outside the enclosure to within the enclosure, and
   pressure control means communicating with the interior of said enclosure for limiting the mximum pressure within said enclosure to a predetermined amount above the ambient pressure outside said enclosure thereby sealing the enclosure against entry of air whereby the jar, the lid and the ring enclosing a food product and held within the enveloping enclosure may be heated within a microwave oven to form steam of the predetermined maximum pressure within the jar to sterilize the food product said pressure control means in combination with said cover member and said jar lid sealing means providing for venting of steam from the jar and from the enclosure, and upon subsequent cooling of the enclosure and the jar causing the pressure within the enclosure and outside the jar to be less than the ambient outside the enclosure and greater than the pressure in the jar, said pressure control means preventing the entry of air into said enclosure, thereby causing the venting of the steam from the jar, again, and to effect an air-tight seal between the lid and the jar when removed from the enclosure.

2. The apparatus of claim 1 wherein said enclosure, base member, and cover member are formed of polysulfone synthetic resin.

3. The apparatus of claim 1 wherein said enclosure includes a water reservoir for holding a small amount of water to be introduced thereinto prior to enclosing the jar and the lid within the enclosure.

4. The apparatus of claim 1 wherein the lid and the ring are of metallic material.

5. The apparatus of claim 1 wherein the lid and the ring are of a non-metallic material.

* * * * *